(12) United States Patent
Druery et al.

(10) Patent No.: US 6,807,697 B2
(45) Date of Patent: Oct. 26, 2004

(54) POSTURAL PILLOW

(76) Inventors: Annie Roelofina Druery, 20841 Warden Ave., Queensville, Ontario (CA), L0G 1R0; Andrew Stuart Arthur Holland, 56 Seaton Dr., Aurora, Ontario (CA)

(*) Notice: Subject to any disclaimer, the term of this patent is extended or adjusted under 35 U.S.C. 154(b) by 0 days.

(21) Appl. No.: 10/059,231

(22) Filed: Jan. 31, 2002

(65) Prior Publication Data

US 2004/0172761 A1 Sep. 9, 2004

(51) Int. Cl.[7] .............................................. A47C 20/00
(52) U.S. Cl. ................... 5/650; 5/648; 5/640
(58) Field of Search ..................... 5/648, 650, 637, 5/640, 636, 643, 657; 128/845, 882

(56) References Cited

U.S. PATENT DOCUMENTS

| | | | | |
|---|---|---|---|---|
| 4,060,863 A | * | 12/1977 | Craig | ............................ 5/644 |
| 4,177,806 A | | 12/1979 | Griffin | |
| 4,447,922 A | * | 5/1984 | Brochu | ........................... 5/637 |
| 4,736,477 A | | 4/1988 | Moore | |
| 4,777,678 A | * | 10/1988 | Moore | ........................... 5/657 |
| 5,216,771 A | | 6/1993 | Hoff | |
| 5,418,991 A | | 5/1995 | Shiflett | |
| 6,145,508 A | | 11/2000 | Seip, Jr. | |
| 6,182,311 B1 | * | 2/2001 | Buchanan et al. | ............. 5/632 |

* cited by examiner

Primary Examiner—Michael F. Trettel

(57) ABSTRACT

A postural pillow for spacing apart a user's knees when the user is in a lateral recumbent position. The pillow is kidney-shaped, rendering it useful as both a knee pillow and as a cervical pillow for supporting the head and neck. The pillow is provided with two lateral straps positioned about the user's calf for securing the pillow to the knee area. A third strap extends longitudinally, fitting over the user's lower thigh just above the knee so as to prevent the pillow from slipping down the user's leg. The straps ensure the pillow remains in place between the user's knees when at rest or walking, while minimizing the tension placed upon the user's legs by the straps so as to ensure freedom of mobility.

12 Claims, 3 Drawing Sheets

POSTURAL PILLOW

FIELD OF INVENTION

The present invention relates to postural pillows, and specifically to a pillow or cushion adapted to be secured to the inside of a user's leg in the knee area in order to maintain the user's knees in a spaced apart relation.

BACKGROUND OF THE INVENTION

Many people encounter difficulty sleeping in a lateral recumbent position due to discomfort caused by the close proximity of their knees to each other. This discomfort can result from the misalignment of the spine that occurs when a reclining person is positioned on their side or from the physical chafing or bruising caused by knee-on-knee contact. Difficulties are experienced most particularly by individuals with lower back conditions and lower limb conditions, including mechanical low back pain, spondylosis, sciatica, degenerative disc disease, patella femoral syndrome, chondromalacia patella or trochanteric bursitis. Other people that may experience discomfort when in a lateral recumbent position include those with muscular strains or sprains in the back, hip or knee regions, those recovering from medical operations or those with fibromyalgia.

Relief from the discomfort experienced when in a lateral recumbent position is often found by maintaining the knees in a spaced apart relation. This is typically accomplished by placing a pillow, cushion or other soft resilient object between the person's knees when resting or sleeping. Unfortunately, an ordinary pillow or cushion is often incorrectly sized and typically becomes dislodged during sleep.

There are postural pillows designed to provide cervical support for a user when the user is in a sitting position for long periods, such as on an aircraft or train. Cervical pillows are typically shaped so as to provide appropriate support and comfort for the neck and head of the user. It would be advantageous to provide a postural pillow that is adapted for use as both a knee pillow and a cervical pillow.

Various attempts have been made to develop a pillow that can be secured to a user's leg so as to maintain it's location between the knees. U.S. Pat. No. 4,177,806 (Griffin) shows a knee pillow having two lateral straps designed to encircle a person's calf and thigh, respectively, for securing the pillow to the inside of the knee. Likewise, U.S. Pat. No. 4,736,477 (Moore) discloses a knee pillow having two lateral straps adapted to be tightened around a person's calf and thigh. U.S. Pat. No. 6,145,508 (Seip, Jr.) discloses a knee pillow having the same lateral straps as shown in Griffin and Moore. These existing pillows are designed to be strapped transversely around a user's thigh, above the user's knee, in order to secure the pillow in place. Disadvantageously, it is necessary to place such a strap under considerable tension to ensure that the pillow remains in place which results in pressure upon the user's hamstring in both a reclining and standing position. This can cause users discomfort and impede mobility.

Accordingly, there remains a need for a therapeutic pillow that may be secured in position between the user's knees, but that causes minimal discomfort and minimal impairment of movement.

SUMMARY OF THE INVENTION

The postural pillow of the present invention provides a pillow for spacing apart a user's knees including a resiliently deformable body extending longitudinally between a first end and a second end, the body being adapted to be positioned with the first end above the user's knee and the second end below the user's knee; a lower strap having at least one end attached to the body and adapted to be fastened laterally across the user's leg on the lower side of the user's calf muscle, the lower strap extending laterally across the body; an upper strap having at least one end attached to the body and adapted to be fastened laterally across the user's leg on the upper side of the user's calf muscle, the upper strap extending laterally across the body; and a knee strap adapted to be fastened longitudinally across the top of the user's lower thigh, above the user's knee, the knee strap ending longitudinally with respect to the body.

In another aspect, the present invention provides a postural pillow for spacing apart a user's knees that includes a body having a kidney-shape that is adaptable to be employed as a cervical support.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Reference will now be made, by way of example, to the accompanying drawings which show a preferred embodiment of the present invention, and in which.

DETAILED DESCRIPTION OF AN EMBODIMENT

A postural pillow is provided that has a kidney-shaped body and a strapping mechanism for securing the pillow to the user's leg that avoids placing a strap around the user's thigh, thereby obviating forces upon the user's hamstring.

Figure 1:
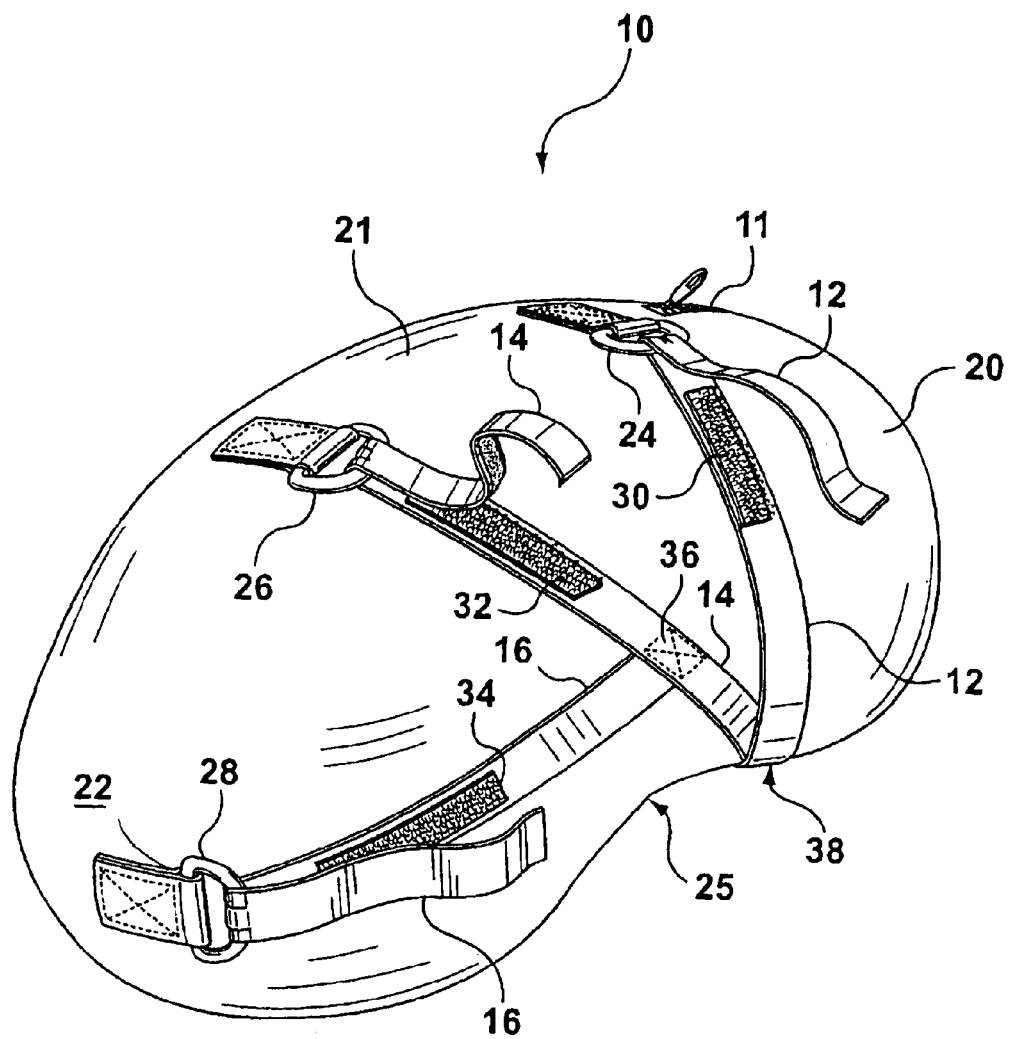
FIG. 1 shows a perspective view of a postural pillow according to the present invention.

Reference is first made to FIG. 1, which shows a perspective view of a therapeutic pillow 10 according to the present invention. The pillow 10 is kidney-shaped, having a profile showing first and second convex ends 20, 22 and a centre portion 21 having a concave underside 25. The concave centre portion 21 together with the convex ends 20, 22 provide a shape well adapted to cradling the user's neck and head when the pillow 10 is in use as a cervical support.

The pillow 10 is formed of a resilient material, preferably a single piece of polyurethane foam, although alternative materials, such as elastomer foam or natural rubber foam, will be apparent to those skilled in the art. The pillow may further include a covering of quilt batting and a polyester-cotton fabric, so as to provide additional comfort. In a preferred embodiment, the pillow 10 is further provided with a washable cover that fits over the quilt batting and polyester-cotton fabric covering. The washable cover may be made of a polyester-cotton fabric, sheepskin or other suitable material. The washable cover is provided with a zipper 11 so as to allow for its easy removal for cleaning or replacement.

The pillow 10 also includes a lower strap 12, an upper strap 14 and a knee strap 16. The lower strap 12 and the upper strap 14 both have one end secured, by stitching, rivet, adhesive or other appropriate fastener, to the pillow 10 at about a bottom point 38 of the first convex end 20. The knee strap 16 has one end secured to the upper strap 14 by stitching, rivet, adhesive or other appropriate fastener. The straps are preferably formed of a thin, flexible, inelastic, non-abrasive material, such as nylon, although other materials may be used such as cotton or polyester.

The straps 12, 14 and 16 are each provided with a strip of a hookable mat material 30, 32 and 34 on their outer surface that cooperatively engages hookable fasteners affixed to the outer surface of the free end of the straps 12, 14 and 16 when the straps are folded back upon themselves. The hookable mat and fastener may, for example, be Velcro™ hook and loop fasteners.

Three D-rings 24, 26, 28 are secured to the pillow 10. The first D-ring 24 corresponds to the lower strap 12 and is located at about the top of the pillow 10 near the first convex end 20. The second D-ring 26 corresponds to the upper strap 14 and is located at about the top of the pillow 10 approximately between the second convex end 22 and the concave centre portion 21. The third D-ring 28 corresponds to the knee strap 16 and is located at about the outer extremity of the second convex end 22. The straps 12, 14 and 16 are adapted to pass through the corresponding D-rings 24, 26 and 28 and be folded back upon themselves to engage the hookable fasteners with the hookable mat material 30, 32 and 34. The D-rings 24, 26 and 28 are preferably formed of a durable rigid material, such as hard plastic or stainless steel.

The D-rings 24, 26 and 28 may be secured to the pillow 10 by a loop formed of a short length of strap fabric passing through the D-ring with both ends stitched to the pillow 10. The short length of strap fabric is preferably formed of the same type of material comprising the straps 12, 14 and 16.

When secured to the D-rings 24 and 26, the lower strap 12 and the upper strap 14 form a V-shape, extending towards the top of the pillow 10. The knee strap 16 is secured to an attachment point 36 of the upper strap 14 at approximately the mid-point of the pillow 10. When secured to the third D-ring 28, the knee strap 16 extends longitudinally between the second convex end 22 of the pillow 10 and the attachment point 36.

The hookable fastners and mat material 30, 32 and 34 together with the D-rings 24, 26 and 28 permit the straps 12, 14 and 16 to fastened at varying adjustable lengths and, accordingly, at varying levels of tension for legs of varying girth.

Figure 2:
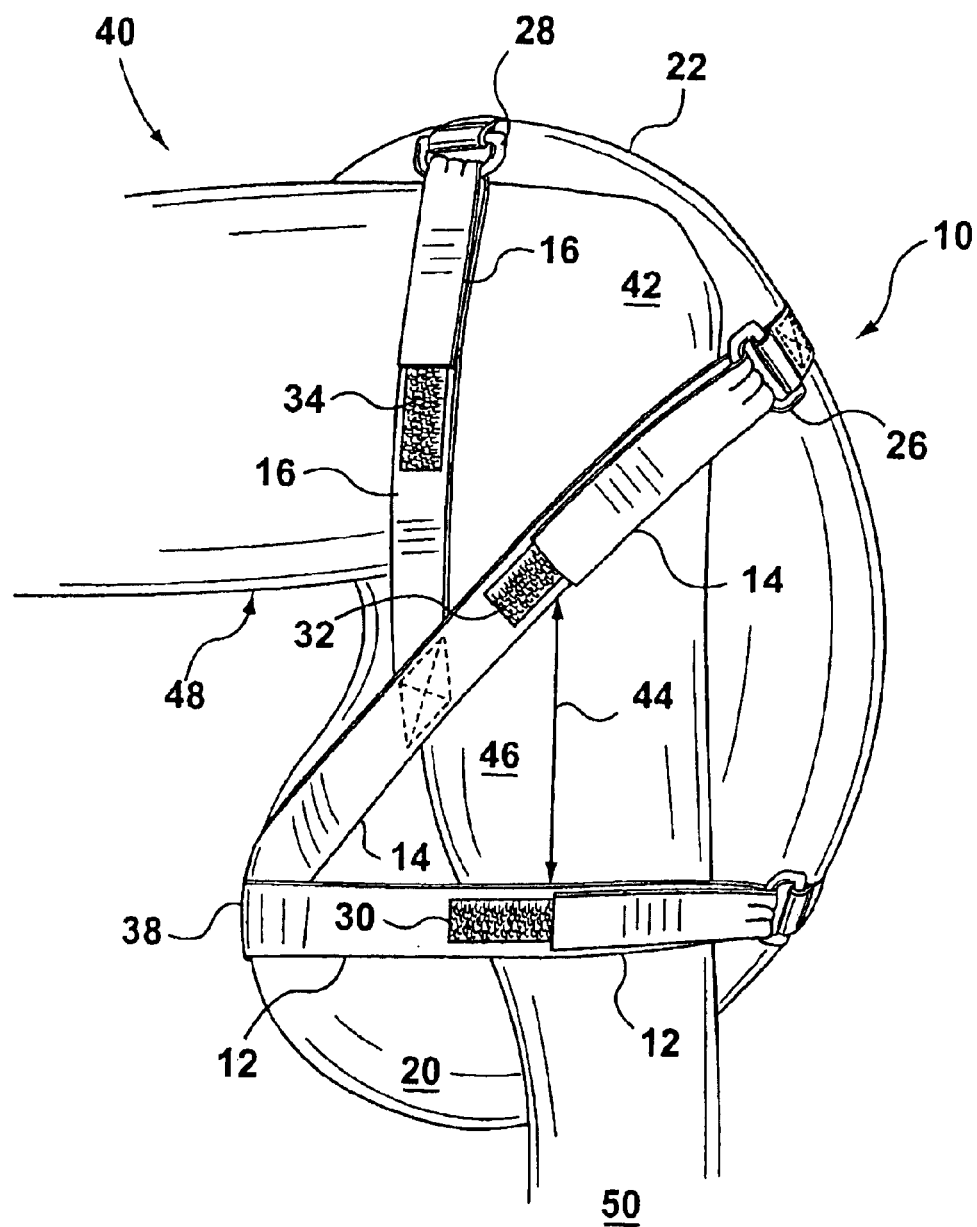
FIG. 2 shows a side view of a postural pillow according to the present invention secured to the leg of a user.

Reference is next made to FIG. 2, which shows the pillow 10 in use by a person as a knee pillow. The person secures the pillow 10 to the inside of their leg 40 using the straps 12, 14 and 16. The lower strap 12 is secured about the person's leg 40 just below the calf muscle 46. The upper strap 14 is secured about the person's leg 40 just above the calf muscle 46 and below the knee 42. The lower strap 12 and the upper strap 14 are spaced apart by a distance 44 within which is located a portion of the calf muscle 46. The calf muscle 46, in cooperation with the upper and lower straps 12 and 14, prevents the pillow 10 from becoming dislodged from the person's leg 40.

The knee strap 16 passes over the top of the person's lower thigh, above the knee 42, and is secured to the third D-ring 28. The knee strap 16 provides longitudinal tension preventing the pillow from slipping down the person's leg 40. The pillow 10 does not require a strap across the back of the person's leg 40, thereby eliminating forces upon the hamstring 48.

When the person is in a lateral recumbent position, the pillow 10 is secured between their knees and the straps 12, 14 and 16 prevent the pillow 10 from becoming dislodged. When the person rises to a standing position, the upper and lower straps 12 and 14 prevent the pillow 10 from falling from the person's leg 40. The knee strap 16 becomes slack and does not place tension upon the knee 42 when the person is in a standing position. Accordingly, the person is afforded great freedom of movement. There is no strap secured around the person's thigh placing tension upon the hamstring 48, which would interfere with normal walking movement.

Advantageously, the pillow 10 of the present invention permits a user to stand and walk without requiring the user to remove the pillow 10 and reattach it when returning to a lateral recumbent position. This is of particular convenience for users employing the pillow 10 at night in circumstances where the user needs to rise briefly.

Figure 3:
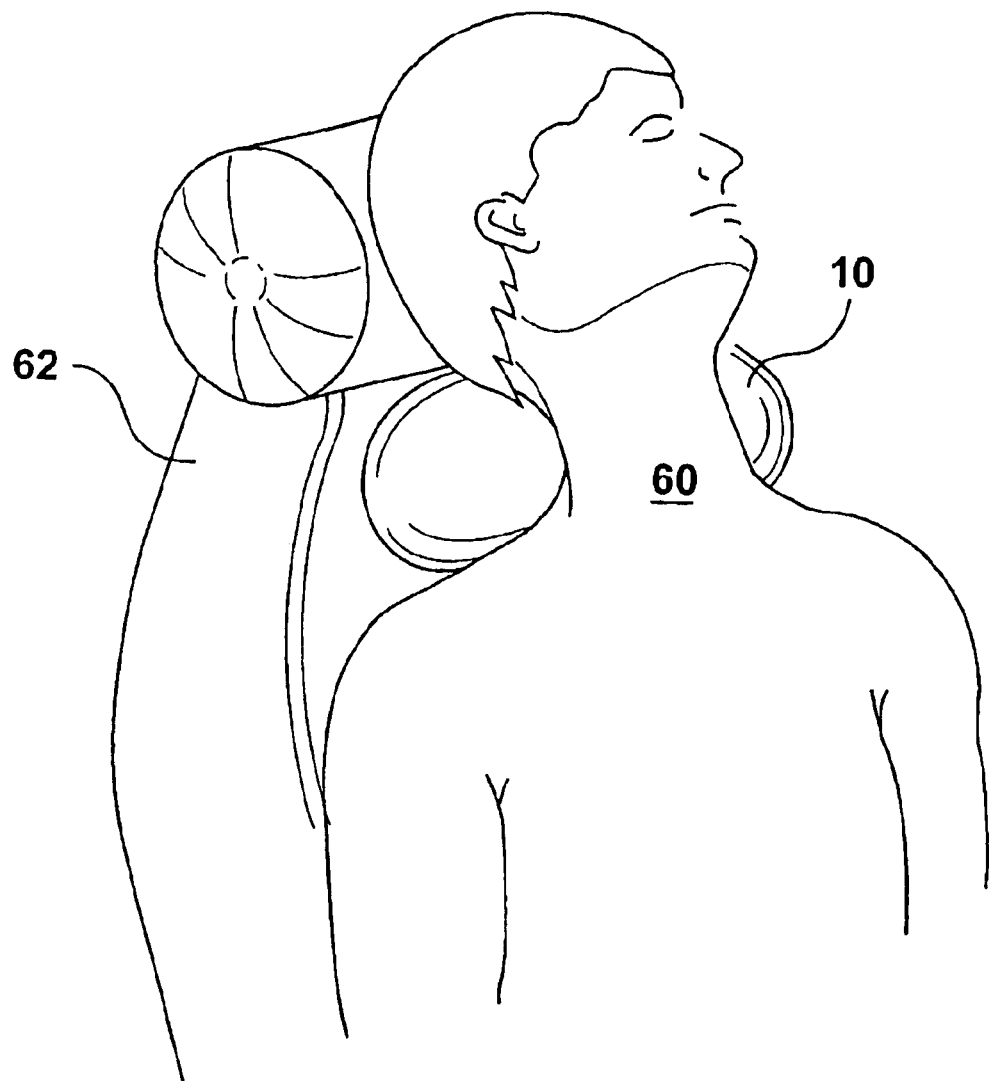
FIG. 3 shows a postural pillow according to the present invention in use as a cervical support.

Reference is now made to FIG. 3, which shows the pillow 10 in use by a person as a cervical support. The person places the pillow 10 behind their neck 60 when in a seated position in, for example, an airline seat 62. The pillow 10 provides support for the person's neck 60 and the lower portion of the person's head. The kidney-shape of the pillow 10 is advantageously suited to mould to the contours of the person's neck 60 and head to provide adequate cervical support.

Although the preferred embodiment described herein discloses strapping mechanisms that included a strap, a D-ring and a hook-and-loop fastener, it will be appreciated by those skilled in the art that various alternative strapping mechanisms may be used. For example, rather than a D-ring and a strap adapted to be passed through the D-ring and fastened to itself, the strapping mechanism could comprise a pair of straps that may be fastened together. Various alternative fasteners may be employed, including snaps, buckles, clips or tape. Those skilled in the art will appreciate the various alternative embodiments.

Although the preferred embodiment is described in an assembled format, it will be appreciated that the invention may be sold, exported, or imported as a kit of parts, with the intention that the user attach the various straps to the body of the pillow prior to use.

The present invention may be embodied in other specific forms without departing from the spirit or essential characteristics thereof. Certain adaptations and modifications of the invention will be obvious to those skilled in the art. Therefore, the above-discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A pillow for spacing apart a user's knees, comprising:
 a resiliently deformable body extending longitudinally between a first end and a second end, said body being adapted to be positioned with said first end above the user's knee and said second end below the user's knee;
 a lower strap having at least one end attached to said body and adapted to be fastened laterally across the user's leg on the lower side of the user's calf muscle, said lower strap extending laterally across said body;
 an upper strap having at least one end attached to said body and adapted to be fastened laterally across the user's leg on the upper side of the user's calf muscle, said upper strap extending laterally across said body; and a knee strap adapted to be fastened longitudinally across the top of the user's lower thigh, above the user's knee, said knee strap extending longitudinally with respect to said body.

2. The pillow claimed in claim 1, wherein said body is kidney-shaped.

3. The pillow claimed in claim 1, wherein said first and second ends of said body are convex ends separated by a concave centre portion.

4. The pillow claimed in claim 1, wherein one end of said knee strap is fastened to said upper strap at approximately the mid-point of said body.

5. The pillow claimed in claim 4, wherein the free ends of said lower strap, said upper strap and said knee strap further include fasteners.

6. The pillow claimed in claim 1, wherein said pillow further comprises three rings corresponding to said straps and fastened to said body, said rings being adapted to receive said straps.

7. The pillow claimed in claim 6, wherein said straps include a hookable fastener affixed to their free ends and a hookable mat material affixed to a middle length of said straps, and wherein, said hookable fastener is adapted to releasably engage said hookable mat material.

8. The pillow claimed in claim 1, wherein said straps each comprise two straps, said two straps being adapted to be releasably fastened together by a fastener.

9. The pillow claimed in claim 8, wherein said fastener is a hook and loop fastener.

10. The pillow claimed in claim 1, wherein said body comprises a resiliently deformable core and a removable washable covering.

11. The pillow claimed in claim 10, wherein said removable washable covering further includes a zipper.

12. A kit of parts for assembling a pillow for spacing apart a user's knees, the pillow comprising:

a resiliently deformable body extending longitudinally between a first end and a second end, said body being adapted to be positioned with said first end above the user's knee and said second end below the user's knee;

a lower strap having at least one end attached to said body and adapted to be fastened laterally across the user's leg on the lower side of the user's calf muscle, said lower strap extending laterally across said body;

an upper strap having at least one end attached to said body and adapted to be fastened laterally across the user's leg on the upper side of the user's calf muscle, said upper strap extending laterally across said body; and a knee strap adapted to be fastened longitudinally across the top of the user's lower thigh, above the user's knee, said knee strap extending longitudinally with respect to said body.

* * * * *